US010835217B1

(12) United States Patent
Gomez et al.

(10) Patent No.: US 10,835,217 B1
(45) Date of Patent: Nov. 17, 2020

(54) ASSEMBLY FOR DOUBLY SECURING NEEDLESCOPIC INSTRUMENT SHAFTS TO LAPAROSCOPIC INSTRUMENT HEADS

(71) Applicant: INNERSPACE SURGICAL CORPORATION, Pompano Beach, FL (US)

(72) Inventors: Ricardo Alexander Gomez, Lighthouse, FL (US); Sandy Lawrence Heck, Los Angeles, CA (US); Eric William Conley, South Berwick, ME (US)

(73) Assignee: NEW WAVE ENDO-SURGERY INC., Coconut Creek, FL (US)

( * ) Notice: Subject to any disclaimer, the term of this patent is extended or adjusted under 35 U.S.C. 154(b) by 867 days.

(21) Appl. No.: 14/975,185

(22) Filed: Dec. 18, 2015

Related U.S. Application Data

(60) Provisional application No. 62/093,789, filed on Dec. 18, 2014.

(51) Int. Cl.
*A61B 17/00* (2006.01)

(52) U.S. Cl.
CPC ............... *A61B 17/00234* (2013.01); *A61B 2017/0042* (2013.01); *A61B 2017/00238* (2013.01); *A61B 2017/00345* (2013.01); *A61B 2017/00367* (2013.01); *A61B 2017/00477* (2013.01)

(58) Field of Classification Search
CPC .. A61B 2017/2931; A61B 2017/00238; A61B 17/00234; A61B 2017/00345; A61B 2017/00473; A61B 2017/00477; A61B 2017/2936; A61B 1/00087; A61B 1/00101
See application file for complete search history.

(56) References Cited

U.S. PATENT DOCUMENTS

| 5,441,059 | A | * | 8/1995 | Dannan | ............ | A61B 17/00234 |
|---|---|---|---|---|---|---|
| | | | | | | 128/898 |
| 5,451,222 | A | | 9/1995 | De Maagd et al. | | |
| 5,830,214 | A | | 11/1998 | Flom et al. | | |
| 6,063,085 | A | | 5/2000 | Tay et al. | | |
| 2005/0125028 | A1 | * | 6/2005 | Looper | .......... | A61B 17/320016 |
| | | | | | | 606/205 |
| 2006/0074432 | A1 | * | 4/2006 | Stad | ...................... | A61F 2/4611 |
| | | | | | | 606/90 |

(Continued)

FOREIGN PATENT DOCUMENTS

WO          9622056          7/1996

OTHER PUBLICATIONS

International Search Report for PCT/US18/16942 dated Mar. 31, 2018.

*Primary Examiner* — Shaun L David
*Assistant Examiner* — Christina C Lauer
(74) *Attorney, Agent, or Firm* — Grogan, Tuccillo & Vanderleeden, LLP

(57) ABSTRACT

The present invention is directed to an assembly used in minimally invasive procedures whereby laparoscopic instrument heads, prepositioned in the abdomen of a patient are securely doubly attached and detached internally while under direct laparoscopic visualization. The present invention permits surgeons to utilize full sized laparoscopic instrument heads on needlescopic instrument shafts. Multiple locking structures are employed to securely attach the laparoscopic instrument heads to a needlescopic instrument.

17 Claims, 6 Drawing Sheets

(56) References Cited

U.S. PATENT DOCUMENTS

| | | | |
|---|---|---|---|
| 2011/0087266 A1* | 4/2011 | Conlon | A61B 17/29 |
| | | | 606/205 |
| 2011/0230853 A1 | 9/2011 | Ihde, II | |
| 2012/0083778 A1* | 4/2012 | McGaffigan | A61B 18/085 |
| | | | 606/28 |
| 2013/0267938 A1 | 10/2013 | Greenberg et al. | |
| 2016/0051408 A1 | 2/2016 | Baerveldt et al. | |

* cited by examiner

ASSEMBLY FOR DOUBLY SECURING NEEDLESCOPIC INSTRUMENT SHAFTS TO LAPAROSCOPIC INSTRUMENT HEADS

CROSS REFERENCE TO RELATED APPLICATIONS

This application claims priority from provisional U.S. Application No. 62/093,789 filed on Dec. 18, 2014 and entitled Method and Apparatus for Securing Laparoscopic Instrument Heads in the Abdomen under Direct Visualization.

FIELD OF INVENTION

The present application is directed toward an assembly used for remotely doubly attaching and detaching laparoscopic instrument heads within the abdomen of a patient to needlescopic instrument shafts under direct visualization.

BACKGROUND OF THE INVENTION

Laparoscopy is a surgical procedure performed through small incisions in the abdomen into which a trocar/cannula device is inserted to provide means for passage of medical instruments. A thin cylindrical instrument called a laparoscope, connected to a camera, is then used to provide a clear picture of the abdominal cavity to the surgeon.

Prior to starting a surgical procedure a small incision is created through the abdominal wall of the patient by a trocar/cannula device into which the device is then inserted. Trocar device diameters range in size from 5 to 12 mm and provide a clear passage for the introduction of medical devices into the abdomen. A device called an insufflator is then used; its purpose is to inflate the abdominal cavity with carbon dioxide and creating a greater working and viewing area for the surgeon. Once the abdominal opening is secured, a special medical viewing device called a laparoscope is inserted through the trocar opening permitting the surgeon to view the abdominal cavity space. Typically, several additional airtight incisions are made ranging in size from 5-12 mm for the introduction of other medical devices The origins of the word Laparoscope can be traced back to the Greek word for "Laparo" meaning "flank". A flank is the side of the body between the ribs and hips commonly referred to as the abdomen and the word "scope" meaning to look at or examine. Hence. Laparoscopes provide means of looking inside the abdomen of a patient The first use of a Laparoscope goes as far back as 400 BC where the physician Hippocrates (460-377 BC) mentioned the use of a device called a rectoscope. A rectoscope was used for inspecting the oral cavity and pharynx of a person. When a tool is used to view the interior of a person thru a natural opening of the body such as the mouth or nose it is more accurately referred to as an endoscope. Laparoscopes and Endoscopes have permitted tremendous strides in the medical field.

It wasn't until 1805 that a physician named Phillip Bozzini of Mainz, Germany invented the Lichtleiter, also referred to as the Bozzini Endoscope. The Lichtleiter consisted of two parts (1) a light container with an optical part and (2) a mechanical part which consisted of viewing tubes adapted to fit inside a body. The Lichtleiter was a tube constructed of various attachments that used concave lenses whereby half of the tube transmitted the light from a candle to the tip of the device and the other half of the opening returned the reflected light showing the surgeon the interior view of the patient. The candle with angled mirrors inside the device provided the light that enabled the physician to see the abdominal cavity. This approach was not practical because of its limitations of maintaining a heated light source, but it was the predecessor of today's laparoscopes and at the time the first device used to inspect the interior of a human body.

Laparoscopy continued to evolve. In 1901 a Doctor by the name of George Kelling performed the first examination of an abdominal cavity (in a dog) by inflating the cavity with gas and then inserting an endoscope. He is often credited with introducing the field of Laparoscopy. In 1910 Victor Elner used a gastroscope to view the interior of a stomach and shortly thereafter a flexible gastroscope was designed. Thereafter in 1911 the first Laparoscopy was performed on a human by the Swedish doctor H. C. Jacobeus. In spite of the technical advances that were being made problems persisted with the heat produced at the tip of the scope when a flame was used for lighting and visualization, causing problems such as blind spots in the field of view. These problems limited the use of Laparoscopy. Its main purpose remained diagnostic.

In the early 20th century with the invention of the light bulb and electrical devices by Thomas Edison, significant advances began taking place. Small light sources could now be attached to the distal tip of Laparoscopes without the need for cooling. The next great evolution happened in the 1950's when significant advances took place in the field of fiber optics. Fiber Optics provided great flexibility and the introduction of smaller light sources into the abdomen without burning the patient.

As surgeries kept evolving, limited interest was focused on minimally invasive type surgeries. It was believed that larger incisions were better. However as some of the many advantages of minimally invasive surgery became apparent such as lower operating cost, less patient trauma, less scarring, less pain, lower surgical complications, quicker recovery times, shortened hospital stays, and less chance of infection, a need developed to find therapeutic uses for Laparoscopy. In the 1970s, thanks to Gynecologists and Gastroenterologists, the use of Laparoscopy began changing from diagnostic to therapeutic uses.

The development of very small high-resolution television cameras and CCD (charged coupled devices) tremendously propelled advances in therapeutic uses. As problems presented themselves inventors focused on solutions that kept Laparoscopic surgeries moving forward. An example of how a problem in laparoscopy led to a great solution is the problem of fogging and visualization that developed in surgery. Inventors such as Ricardo Alexander Gomez, and Dr Sandy Lawrence Heck developed and patented a revolutionary apparatus and method for maintaining laparoscopic lenses crystal clear during procedures and dramatically improved the visualization and effectiveness for these types of surgeries with the use of the apparatus called a D-Help®. Today there is a need in the field for smaller and more effective laparoscopic tools, means of providing direct visualization and methods that minimize the use of additional trocars inserted into the abdominal cavities of patients.

As the field of minimally invasive surgery continues evolving less invasive techniques are desired. The need for smaller Laparoscopic tools has also developed. A newer version of Laparoscopy has evolved called needlescopic surgery. Needlescopic surgery is a progression of laparoscopic surgery whereby incisions smaller than 3 millimeters are made. Virtually no scarring occurs, pain is reduced, and recovery times are faster. However the problem associated with this new type of procedure is the limited functionality of the needlescopic insertion instrument. As the instruments became thinner, the heads of the instruments also became smaller and as a result less effective to manipulate tissues and organs. For this reason among others, needlescopic surgery is not functional for most procedures and has not been widely adopted by the surgical community.

Another new type of surgery called Single Incision Laparoscopic Surgery (SILS) has also been tried to reduce the number of incisions related to surgery. The concept is that a single incision is made at the umbilicus allowing a specialized tool to be placed within the opening. The opening allows the insertion of several very small instrument tools into the abdomen. The problems associated with this procedure are first in the level of complexity for each procedure versus the traditional laparoscopic procedure, the lack of functionality of the smaller tools, and the very tight working area. It is usually limited to only 3 very small instrument devices which often lack the full functionality required by traditional surgeons.

Another new type of surgery used today is called (NOTES) Natural Orifice Translumenal Endoscopic Surgery. It basically involves placing a flexible endoscope through one of the body's natural orifices, like the mouth, anus, vagina, or urethra. Its purpose is to allow access to a space near the affected area. Some of the problems associated with this type of surgery are that the number of instrument heads used is usually limited to only one, not all areas of the body are accessible, and, since most views are in two dimensions, there are special orientation problems.

An additional problem associated with both Single Incision Laparoscopic Surgery (SILS) and Natural Orifice Translumenal Endoscopic Surgery (NOTES) is their lack of ability to achieve triangulation. Triangulation in this instance is defined as the ability to come at a target from different directions or angles. Triangulation provides significant benefits to the surgeon, among them are: effective control of the surgical procedure and the ability to better manipulate internal body parts. When this ability is lost it is difficult to effectively perform the set types of surgeries. This is one of the reasons that have prevented SILS and NOTES from becoming widely adopted. The technology described herein solves this problem by facilitating triangulation from many directions, a feature that is lost in both SILS and NOTES.

People have experimented with the concept of attaching larger instrument heads to thin needlescopic instrument shafts inside the body under direct visualization as disclosed in copending U.S. application Ser. No. 14/849,833, entitled Needlescopic Instrument System, filed Sep. 10, 2015 by the same inventors, the teachings of which are incorporated herein by reference. This application differs from the previously filed application by accommodating use of a trocar/cannula to support the needlescopic instrument and with the distal end of an inner shaft of the needlescopic instrument engaging the laparoscopic sized head prepositioned within an abdominal cavity of the patient via the trocar/cannula, the engagement being created via a stepped threaded attachment with double locking means for holding the head to the shaft and has to do with method and apparatus for accomplishing same under direct visualization.

These and other aspects, features and advantages of the present invention will become more readily apparent from the attached drawings and the detailed description of the preferred embodiments which follow.

SUMMARY OF INVENTION

The present invention is directed toward devices and a method used in minimally invasive surgery whereby means for securely attaching and detaching laparoscopic instrument heads to needlescopic instrument shafts occurs inside the abdomen of a patient, under direct visualization, and while providing a support system for the needlescopic instrument shaft in the form of a trocar/cannula insertion device.

After one or more laparoscopic instruments heads are inserted and suitably deployed inside the abdomen of a patient for attachment to a needlescopic instrument shaft, a particular attaching procedure is performed. This procedure secures the instrument head to the shaft via threading and locking, under direct visualization, while the shaft is supported by a trocar/cannula. This procedure permits the use of larger instrument heads and smaller diameter shafts. The shaft incorporates a permanent or disposable distal piercing tip that permits piercing of the skin. The uniqueness of the distal piercing tip is that not only does it help insert itself into the abdomen but it also provides a means for its secure attachment to a laparoscopic instrument head. With the introduction of multiple locking features for securing the instrument head to the shaft, better attachment.

The present invention is intended to reduce incision sizes and number of trocars used, while still providing for use of full sized laparoscopic instrument heads. This is achieved by using a thin shaft having a sharp tip that smoothly pierces the abdominal skin and is attachable to a laparoscopic instrument head. The thin shaft is between 1-4 mm in diameter, preferably 2 mm, and leaves a needle sized scar that would not be visible to the naked eye. Typically these needlescopic instrument shafts include a needlescopic instrument head already attached to the distal end of an inner shaft comprising a rod. As the shafts become thinner so do their corresponding instrument heads. This reduction in size reduces significantly the functionality of the instrument head, and becomes a disadvantage in its use. The present invention solves this problem by permitting the use of multiple thin shafts that virtually leave no scarring while providing for the use of full sized laparoscopic instrument heads. Excellent functionality of the heads is achieved, while direct visualization is maintained throughout the attachment and detachment procedure.

According to one embodiment of the present invention there is provided a small-diameter needlescopic instrument for use in minimally invasive and needlescopic surgery with a shaft having a sharp piercing distal tip. The instrument shaft is capable of being inserted through the abdominal wall without the need for a trocar (although small trocars could be used if desired). The distal tip of the instrument shaft is capable of attachment to laparoscopic heads already inserted into the body cavity through a trocar. The needlescopic instrument shaft comprises two elongate sections, an inner shaft and an outer shaft. Both shafts have control handles, or grips, at their proximal ends, used for providing functionality such as opening, closing, rotating, extending, retracting, stapling, clipping and/or otherwise activating the laparoscopic instrument head after being functionally engaged to the needlescopic instrument shaft, the shafts thereof providing control means along their longitudinal axes.

The inner shaft of the needlescopic instrument attachment device extends along its longitudinal axis from a proximal end of the shaft to its pointed distal end. The distal end of the inner shaft has a sharp tip designed to pierce the skin and further provides adjacent means for attachment to an embedded laparoscopic instrument head. The inner shaft is attached to an instrument handle used to control the extension, retraction and/or rotation of the inner shaft relative to the outer shaft and for locking the laparoscopic instrument head to the inner shaft. An inner shaft external distal control knob can be used to rotate the distal tip for securement to the laparoscopic instrument head. An outer shaft external distal knob is also incorporated on the outer shaft, providing means for rotating the outer shaft along its longitudinal axis for securement purposes as well.

The distal end tip of the inner shaft has tapered pointed locking means having a stepped screw threaded configuration. This configuration is used to engage the proximal end of a laparoscopic head to the shaft rod. A secondary means of attachment not limited to but employing a threaded locking mechanism may then be used. Here the threads of the inner shaft rod are securely held in place by rotating the inner shaft rod's proximal knob in one direction and the outer shaft's proximal knob in the opposite direction, providing at least two locking means. Other embodiments may use one or more attachment combinations such as pressure fit, magnets, clips, locks, hinges or loops to secure the laparoscopic head to the shaft rod. Not limiting but among devices used to secure the shaft rod to the instrument head are push locking features with two or more locking members, a tube latch device with an open or closed end locking feature. A Disk latching device not limited but constructed of metal, metal alloys, aluminum or plastics may also be used, having extendable side metal wings that bend downward and outward as the distal threaded tip protrudes outward securing the distal end of the tip as it moves further into the locking mechanism. Another locking feature that may be used is a molded latch device. This locking structure is typically made of but not limited to plastic like materials, having a recessed opening at its center capable of securely holding the distal tip of the threaded rod. The invention is not limited to these configurations but may employ various combinations thereof or other industry standard locking devices.

In another embodiment simple push twist connection means are employed for locking the outer shaft to the instrument head. The threads behind the distal piercing tip of the inner shaft provide second locking means. This embodiment can be made of but not limited to aluminum, metal, metal alloys, hard plastics or other standard medical device materials.

In different embodiments, the internal mechanisms of exemplary laparoscopic instrument head attachment apparatuses are shown. The basic concept consists of a threaded tip of an inner shaft being attached to an internal moving/locking mechanism. This mechanism transfers the pushing and pulling actions of the threaded inner shaft tip to opening and closing actions of the attached laparoscopic instrument head.

Preferably, a minimum of two locking structures are necessary for securing the laparoscopic instrument head to the needlescopic instrument shafts of the present invention; one locking the inner shaft to the head, and another locking the outer shaft to the head using direct visualization.

It will be understood that all the structures in the abdomen of the patient incorporate radio opaque material markers for ease in finding them for removal.

It should be noted that in laparoscopic surgery direct visualization is achieved through the use of a laparoscope entering and passing through a trocar/cannula. Additional trocars are added in order to insert additional medical instruments. Each additional trocar adds cosmetic scarring to the patient and a higher risk of infection. The present invention solves these problems by using an insertion deployment device that introduces laparoscopic instrument heads into the abdomen with a thin needlescopic shaft (2 mm) being securely attached to the head while under direct visualization, with all structures being supported and stabilized by a single trocar such that no further trocars/cannula's are needed.

Direct visualization is achieved by having the laparoscopic heads already deployed in the trocar, permitting the camera to maintain direct visualization of the entire process.

Important distinctions when using exterior attachment controls for internally attaching a laparoscopic instrument head are ease of use and good feedback resistance. The ease of use facilitates the surgeon's use and the feedback resistance helps the surgeon achieve better dexterity in the form of feeling the process.

Another unique feature of the present invention is that the laparoscopic heads are supported and stabilized by and within the trocar. The trocar holds the heads securely against movement providing a specific location for each head, and provides a stable platform for direct visualization thereof.

There is a need in the field for a functional apparatuses that allows a user to maintain direct visualization while attaching and detaching laparoscopic instrument heads within the abdomen of a patient, such as to endoscopic or needlescopic shafts used in Laparoscopic surgery. The attachment means must incorporate two or more locking structures to secure the laparoscopic head to the needlescopic instrument shafts while under direct visualization. These and other aspects of the present invention will become more readily apparent from the attached drawings and the detailed description of the preferred embodiments which follow.

BRIEF DESCRIPTION OF DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower". "left", "rear", "right". "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.*

Figure 1:
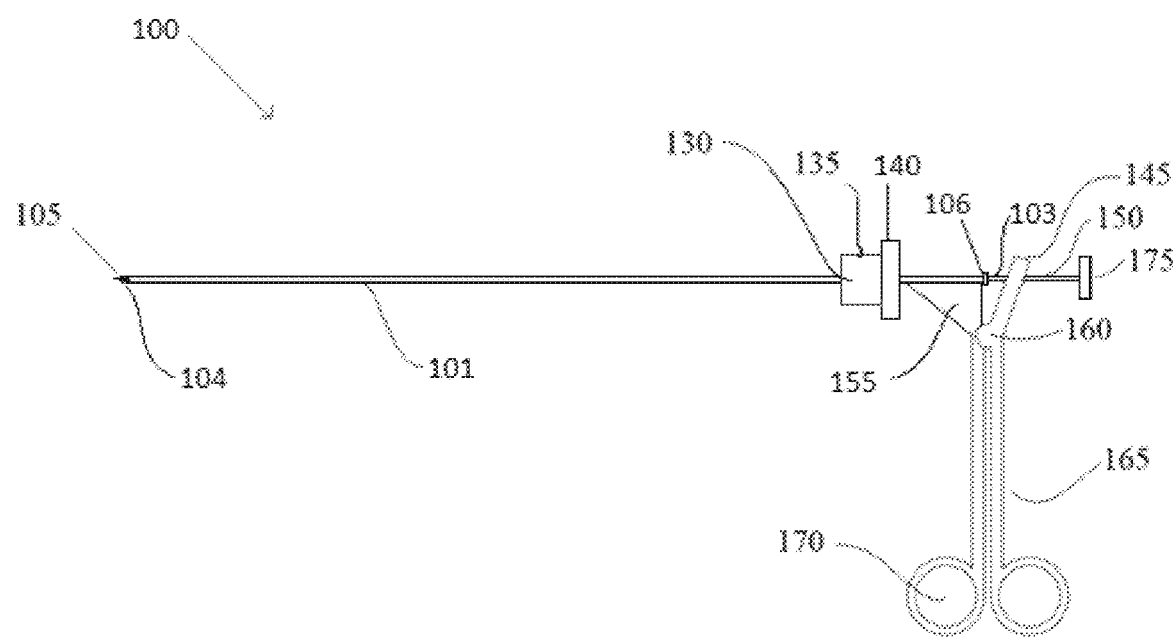
FIG. 1 presents an isometric view of an exemplary needlescopic apparatus which is secured to laparoscopic instrument heads, both the apparatus and exemplary head being made in accordance with the teachings of the present invention.
Figure 5:
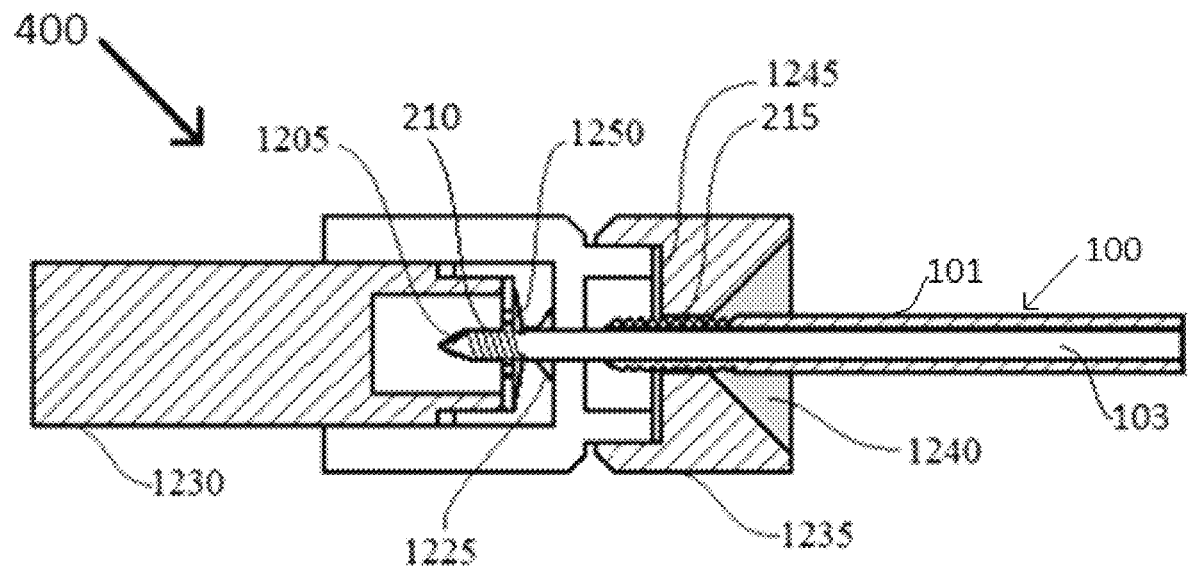
FIG. 5 presents a cross sectional view of the structures of FIGS. 1 and 4 connected into their functional state

With respect to FIG. 1 a needlescopic instrument (100) which engages laparoscopic instrument head (1230) of FIG. 5, previously positioned within the abdomen of a patient, under direct visualization, is presented. The needlescopic instrument (100) includes a hollow outer shaft (101) and an inner shaft or rod (103) having at its distal end (104) a Distal Piercing Tip (105) used for piercing through the skin and for engaging a desired laparoscopic Instrument Head (1230) of FIG. 5. The length of the Outer Shaft (101) can vary depending on the patient and type of surgery performed. The Outer Shaft (101) extends from the distal end (104) to a proximal end (106) where it engages a Handle Attachment Body (155). An Outer Shaft Rotational Hub (130) provides a means of rotating the hollow outer shaft (101) of the needlescopic instrument (100) via a Rotation Knob (140). A Locking Screw (135) is employed to securely fasten the Outer Shaft (101) to the Outer Shaft Rotational Hub (130). The Handle Attachment Body (155) is used to connect the needlescopic instrument (100) to a Handle (165) used in controlling deployment of the Inner Shaft or rod (103). A Pivot (160) is provided to permit lateral movement of the Inner Shaft or rod (103) relative to the movement of the Handle (165). An inner Shaft Insertion Controller (145) engaged at a proximal end (150) of the inner shaft or rod (103) and operated via a scissor like structure (170) functionally engaged to the Inner Shaft Insertion Controller (145) provides a physical connection to the distal end (104) of the Inner Shaft (103). An Inner Shaft Rotation Knob (175) is located at the proximal end of the inner shaft (103) and provides a means of controlling the rotational movement of the inner shaft or rod (103) about its longitudinal axis. The rotation knobs (140 and 175) and handle (165) are used to activate or deactivate features of the laparoscopic instrument head (1230), either through rotation, depression, extension, or any other suitable means of manipulation.

Figure 2:
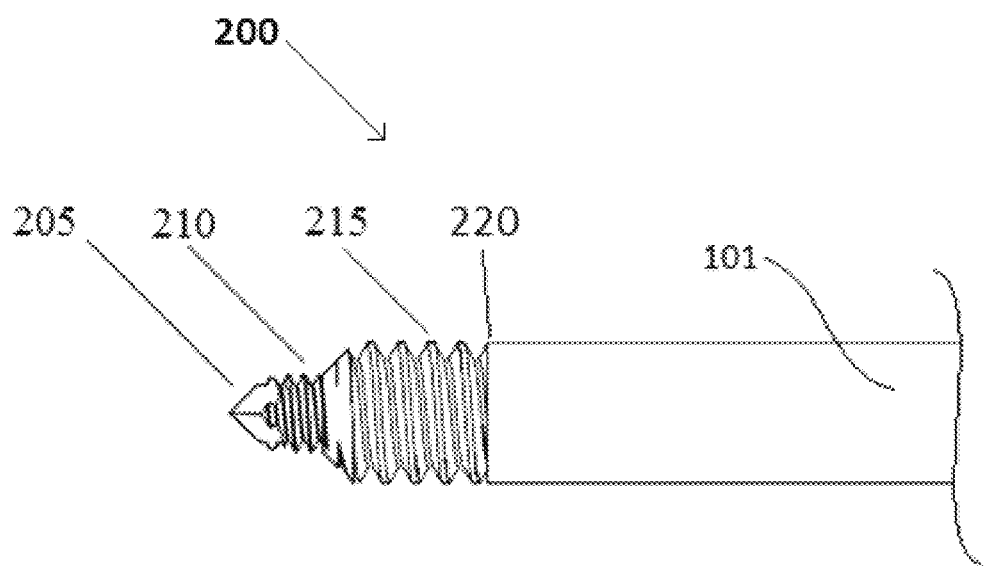
FIG. 2 presents an isometric side view of the distal ends of the threaded tips of an inner and of an outer shaft of the apparatus of FIG. 1.

With respect to FIG. 2 a Distal End Double Locking Stepped Threaded Tip (200) is presented. A Distal Piercing Tip (205) thereof is used to pierce through the skin of a patient. A narrower Inner Shaft Locking Thread (210) makes a first connection with a laparoscopic Instrument Head (not shown) and a secondary locking device using a wider Outer Shaft Locking Thread (215) makes a second connection with the laparoscopic Instrument Head (not shown FIG. 5, 1230). A Distal end (220) of the Outer Shaft (101) provides cover for a remaining portion of the inner Shaft Locking Thread (210).

Figure 3:
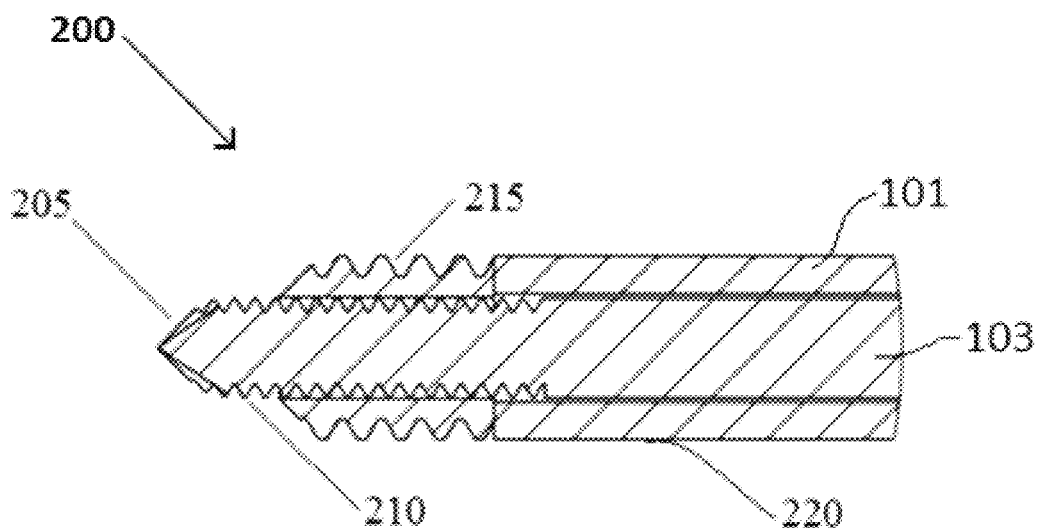
FIG. 3 presents a longitudinal cross sectional view of the threaded tips of the inner and outer shafts of the apparatus of FIG. 1, a distal end of the inner shaft fitting snugly within the distal end of the outer shaft.

FIG. 3 shows in cross section how the narrower Inner Shaft Locking Thread (210) behind the distal piercing tip (205) is slidably received within the outer shaft locking thread (215) area of the Outer Shaft Distal End (220) and how the Outer Shaft Distal End (220) is closely fitted about inner shaft locking thread (210) but remains independent thereof.

Figure 4:
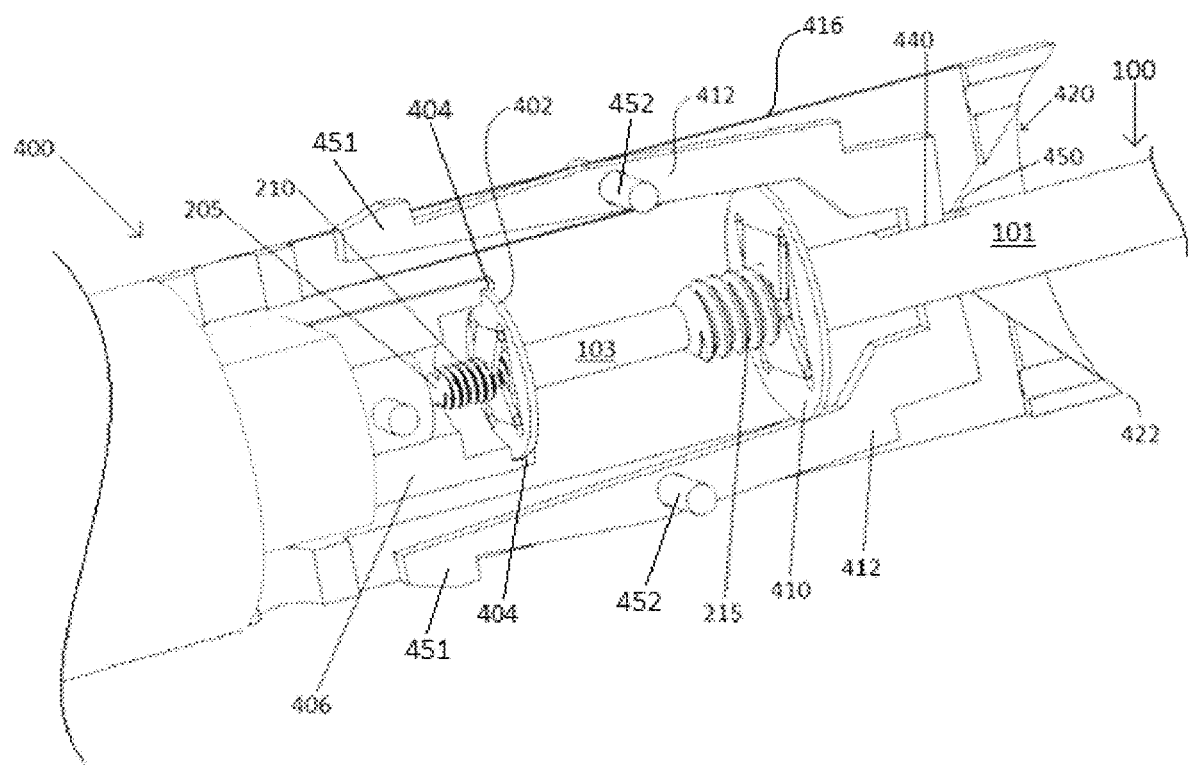
FIG. 4 presents a cross sectional view through a laparoscopic head incorporating dual locking structures for engaging of the apparatus of FIG. 1 securely thereto.

Turning now to FIG. 4, the double locking laparoscopic head (400) makes a unique double click sound as the outer and inner needlescopic shafts (101) and (103), respectively, are inserted into the laparoscopic head 400 and attached thereto. The head 400 has several critical components contained within it. A inner shaft H-clip (402) fixed within opposite slots (404) engages threads of the Inner Shaft locking thread (210) located at the distal end of the inner shaft 103 to provide means for producing a pulling force to close jaws (not shown), for example, of a jaw-like embodiment of a laparoscopic head 400. A second H-clip 410 is engaged to and between pivotable anti-rotation levers 412 pivotably engaged to an outer wall 416 of the double locking laparoscopic head 400 and engages the outer shaft locking thread (215) of the hollow outer shaft 101, providing a constant position for the double locking laparoscopic head 400 in relation to the needlescopic instrument (100) and provides a force for opening and closing, for example, jaws (not shown) of the double locking laparoscopic head (400) as required. The pivotal anti-rotation levers (412) also provide means by which the double locking laparoscopic head (400) is prevented from rotating around the central axis. This is important as it prevents the double locking laparoscopic head (400) from accidentally disconnecting during use and allows the user to grasp tissue and torque or twist it. It will be understood that a jaw-like head (not shown) also contains several levers and pivot points (452) which allow the jaws to open and close, as provided in most laparoscopic graspers and scissors and known in the art.

When the needlescopic instrument shafts 101 and 103 are initially inserted into a Conical opening (420) in a proximal end (422) of the laparoscopic head (400) the distal piercing tip (105) of the inner shaft (103) first passes through the outer shaft H clip (410) and the outer shaft (101) first engages clip 410, providing first means for connection. The outer shaft H-clip (410) functions by opening over the threaded end (215) of the outer shaft (101). The Outer shaft H-clip (410) allows the hollow outer shaft (101) to enter into it by spreading the locking tabs 610 (FIG. 5) of the Inner shaft H-clip (402) to open. Edges 622 (FIG. 6) of a central opening 603 (FIG. 6) in the outer shaft H-clip (410) then bite down into the threads (215) of the outer shaft (101) if the Needlescopic instrument (100) is pulled proximally.

The next step in connecting the Needlescopic Instrument (100) to the double locking laparoscopic head (400) is opening the handle (165) slightly. This drives the inner shaft (103) forward into and through the Inner shaft H-clip (402). The Inner shaft H-clip (402) is identical in function to the outer shaft H-clip (410) and similarly bites down into the threads (210) on the inner shaft (101) as it passes through the inner shaft H-clip 402. The process of making these two connections makes two distinctive clicks signaling a double, appropriate and secure connection has been made.

Once the two shafts have been clicked into position, the user then withdraws the double locking laparoscopic head (400) from a delivery system (not shown) within the abdominal cavity, under laparoscopic visualization, as described in applicant's copending U.S. application Ser. No. 14/849,833, the teachings of which are incorporated by reference. This allows the user to remove the delivery system from the abdomen and begin using the laparoscopic head doubly attached to the inner and outer needlescopic shafts 103 and 101, respectively.

The third step in making a complete connection requires a slight rotation of the Double locking laparoscopic head 400 on the Inner shaft (103) which is manually accomplished. The two points (440) of the anti-rotation levers (412) press down against the outer shaft 101. When the head 400 is in the delivery system the levers 412 are lifted away from the shaft 101 allowing it to rotate freely. When the outer shaft (101) is rotated in the double locking laparoscopic head (400), points 440 on the levers align with slots (450) machined into the outer hollow shaft (101). The points (440) now drop into the slots (450) and once positioned in the slots 450 the double locking laparoscopic head (400) is no longer able to rotate. This keeps the double locking laparoscopic head (400) from accidentally rotating and disconnecting from the needlescopic shafts 101, 103 while in use. This part of the connection process is blind to the user, and during typical use, the user will not need to actively engage the anti-rotation levers (412).

Once the points (440) of the anti-rotation levers (412) are disengaged from the slots 450, the user can now remove the shafts 101,103 from engagement within the Double locking Laparoscopic head (400) by rotating the inner shaft (103) counterclockwise. After several rotations the inner shaft (0.103) will disconnect from the inner shaft H-clip (402) and slide back into outer shaft (101). Then the user can rotate the hollow outer shaft (101) several rotations until the hollow outer shaft (101) disconnects from the outer shaft H-clip (410) and the needlescopic instrument (100) can now be removed from the double locking laparoscopic head (400). The needlescopic instrument (100) can now be removed from the abdomen by gently sliding it out and the head delivery system is then removed, removing the double locking laparoscopic head (400) from within the abdomen as well.

With respect to FIG. 5, a cross sectional view of the embodiment 400 of FIG. 4 is presented showing all the structures joined together for use in the preferred embodiment of this invention. A distal piercing tip (1205) forming a part of the inner shaft (103) is inserted into the Double Push Locking Mechanism (400). It passes through a laparoscopic Instrument Proximal End Guide (1240) to the Primary Locking structure (1250). Subsequently when the user is ready to remove the double locking laparoscopic head (400) from the needlescopic instrument (100) at the end of the procedure requiring that particular double locking laparoscopic head (400), the user reinserts the double locking laparoscopic head (400) into the head delivery system (not shown). The inserting of the double locking laparoscopic head (400) into an opening (not shown) in the head delivery system lifts the points 440 of FIG. 4 of the anti-rotational levers (412) out of the slots (450) in the hollow outer shaft (101), thereby disengaging the double locking laparoscopic head (400) from the anti-rotation levers (412). This takes place when the distal flanges (451) of the anti-rotational levers (412) are pushed inwardly by the opening (not shown) for receiving the double locking laparoscopic head (400) back into position within the head delivery system. The anti rotational levers (412) are pivoted about pivot points (452) which are spring loaded (not shown) to keep the points (440) inwardly biased until released through engagement with the head delivery system, distal piercing tip (1205) is guided to the Primary Locking Structure (1250) by means of the Distal Tip Guide (1225). The Primary Locking structure (1250) can be configured to any suitable shape such as those referred to above. The locking structures form part of what is referred to as a Double Push Locking Mechanism (400) and can be constructed of various metals and or metal alloys, Plastics, or other industry standard materials. Once the Distal Piercing Tip (1205) is secured, a second securing structure is actuated. The Outer Shaft Threaded Portion (215) is rotated through the Outer Thread Locking Mechanism (1245) via the Inner Shaft Rotational Knob (175) of FIG. 1. Removal of the double push locking mechanism (400) is achieved by performing the procedures in reverse.

Figure 6:
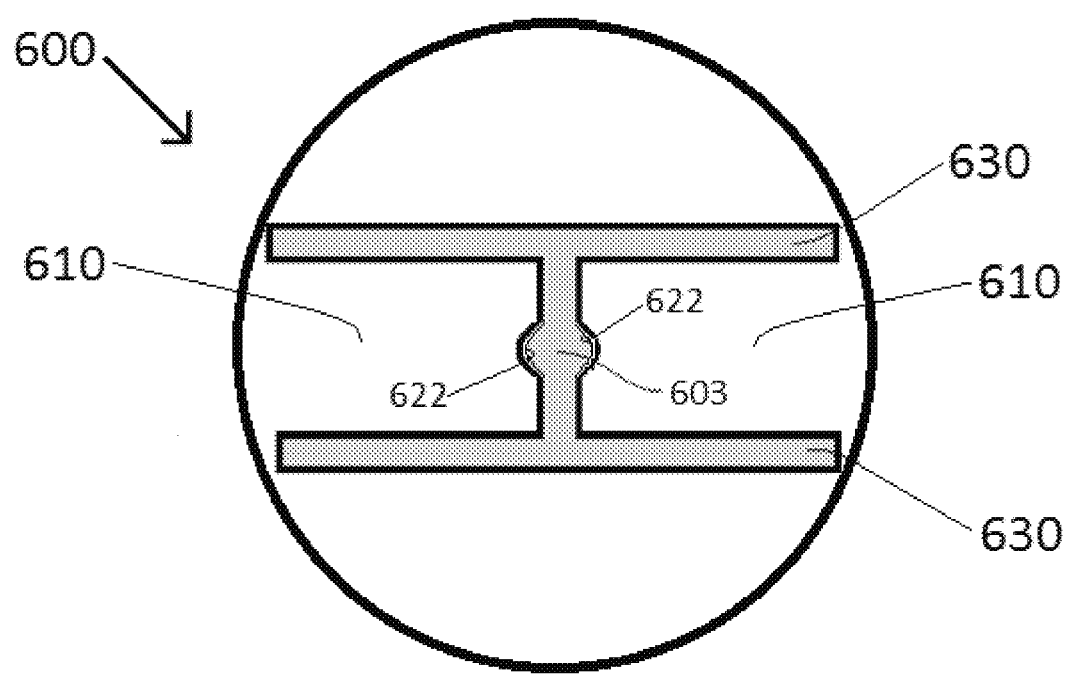
FIG. 6 presents a top plan view of a disk latching device of the head.

Locking tabs (610) formed between parallel cutouts (630) surrounding Outer Shaft Guide opening (603) in the shape With respect to FIG. 6, a DISK latching or Locking Mechanism (600) is presented illustrating how it may be used in a different embodiment of this invention to securely engage a laparoscopic Instrument Head (not shown). An Outer Shaft Guide Opening (603) located at the disk's center, permits the Inner Shaft (620) not shown to pass through the Outer Shaft Guide opening (603) and permits the Inner Shaft (620) not shown to be locked in position H-clip (402) of FIG. 4, which allows the locking tabs (610) to deform into the position shown in FIG. 4.

An assembly for use in needlescopic surgery wherein a needlescopic instrument is doubly engaged to a laparoscope sized instrument head seated within a body cavity, the assembly being created within the body cavity under direct visualization, the assembly comprising, a needlescopic instrument comprising inner and outer shafts, the inner shaft incorporating a cutting edge at a distal end thereof with a screw threaded section proximally adjacent thereto, and the outer shaft fitting about and over the inner shaft and including a threaded distal end, the inner and outer shafts having structures on their proximal ends for use in maneuvering the shafts as necessary, independently of one another, and a laparoscope sized instrument head incorporating at a proximal end thereof, first needlescopic instrument engaging structure for engaging the threaded portion of the outer shaft and second needlescopic instrument engaging structure for engaging the threaded portion of the inner shaft, the inner shaft extending further distally within the proximal end of the laparoscope sized instrument head, thereby creating a doubly engaged assembly comprising the needlescopic instrument and the laparoscope sized instrument head.

The assembly of claim 1 wherein the first and second engaging structures for engaging the threaded portions of the inner and outer shafts comprise clips which engage threads of the threaded portions against disengagement upon exertion of a proximal pulling force. The assembly of claim 1 wherein the distal end of the inner shaft is functionally engaged to the functional structure at the distal end of the laparoscope sized instrument head via clockwise threading of the threaded portion of the inner shaft thereto. The assembly of claim 1 wherein the outer shaft is fixed against rotation by the first needlescopic instrument engaging structure in the laparoscope sized head engaging the shaft when the threaded distal end of the outer shaft is appropriately engaged by the structure engaging the threads thereof.

The assembly of claim 1 wherein the proximal end of the inner shaft is engaged to a handle for controlling insertion and extraction thereof and also to a rotation knob for controlling rotation of the inner shaft.

The assembly of claim 1 wherein the proximal end of the outer shaft is engaged to a control hub in fixed relationship thereto for controlling insertion and extraction and for controlling rotation of the outer shaft.

The assembly of claim 1 wherein the first and second needlescopic engaging structures are fixed in place within the laparoscope sized head.

The assembly of claim 1 wherein the outer shaft is rotatable into engagement with the proximal end of the laparoscope sized head so both rotate together until disengaged from one another.

The assembly of claim 2 wherein creation thereof is confirmed by the sound of two clicks when the first and second clips each respectively engage their cooperating needlescopic instrument shaft.

A method for creating and using an assembly in needlescopic surgery wherein a needlescopic instrument is doubly engaged to a laparoscope sized head already positioned within a body cavity, and the assembly being created under direct visualization and wherein the assembly comprises: a needlescopic instrument comprising inner and outer shafts, the inner shaft incorporating a cutting edge at a distal end thereof with a screw threaded section proximally adjacent thereto, and the outer shaft fitting about and over the inner shaft and including a threaded distal end, the inner and outer shafts having structures on their proximal ends for use in maneuvering the shafts as necessary, independently of one another, and the method of creating the assembly including the steps of: creating a cut with the cutting edge of the inner shaft into the body cavity wherein the laparoscopic instrument head is already positioned for engagement to the needlescopic instrument, under direct visualization, pushing the needlescopic instrument through the delivery system for the laparoscope sized instrument head and engaging the threaded portion of the outer shaft to the first thread engaging structure and creating a rotational engagement between the outer shaft and the laparoscope sized head so both rotate together, pushing the inner shaft of the needlescopic instrument distally of the distal end of the outer shaft and into engagement with the second thread engaging structure and rotating the inner shaft clockwise for engagement to operational structures for functionality of the distal end of the laparoscope sized head, and using the head for the particular purpose for which it was designed.

The method of claim 10 wherein the creation of the double engagement between the inner and outer needlescopic instrument shafts and their respective clips is indicated by two clicks.

A method for deconstructing an assembly in needlescopic surgery wherein a needlescopic instrument is doubly engaged to a laparoscope sized head already positioned within a body cavity, and the assembly being created under direct visualization and wherein the assembly comprises: a needlescopic instrument comprising inner and outer shafts, the inner shaft incorporating a cutting edge at a distal end thereof with a screw threaded section proximally adjacent thereto, and the outer shaft fitting about and over the inner shaft and including a threaded distal end, the inner and outer shafts having structures on their proximal ends for use in maneuvering the shafts as necessary, independently of one another, and a laparoscope sized instrument head engaged to a delivery system therefor positioned within a body cavity and incorporating at a proximal end thereof, first needlescopic instrument engaging structure for engaging the threaded portion of the outer shaft and second needlescopic instrument engaging structure for engaging the threaded portion of the inner shaft, the inner shaft extending further distally within the proximal end of the laparoscopic instrument head, thereby creating a doubly engaged assembly comprising the needlescopic instrument and the laparoscope sized instrument head, the method of creating the assembly including the steps of: inserting the laparoscope sized instrument head back into the delivery system for same by pushing the needlescopic instrument through an opening in the delivery system for passing the instrument through and repositioning the laparoscope sized instrument head within the delivery system, the head including biased side tabs which are pressed inwardly as the instrument passes through the opening therefor, the pressing inwardly of the side tabs releasing a rotational engagement between the outer shaft and the laparoscope sized head, pulling the inner shaft of the needlescopic instrument proximally into the distal end of the outer shaft and out of engagement with the second thread engaging structure by rotating the inner shaft counterclockwise for disengagement from operational structures for functionality of the distal end of the laparoscope sized head, pulling the outer shaft of the needlescopic instrument proximally and out of engagement with the first threaded structure by counterclockwise rotation thereof, and disengaging the instrument head within the delivery system therefor from the needlescopic instrument.

As will be recognized by those of ordinary skill in the pertinent art, numerous modifications and substitutions can be made to the above-described embodiments of the present invention without departing from the scope of the invention. Accordingly, the preceding portion of this specification is to be taken in an illustrative, as opposed to a limiting sense.

What is claimed is:

1. An assembly for use in needlescopic surgery wherein a needlescopic instrument is doubly engaged to a laparoscope sized instrument head seated within a body cavity, the assembly being created within the body cavity under direct visualization, the assembly comprising, a needlescopic instrument comprising inner and outer shafts, the inner shaft having a cutting edge at a distal end thereof and a screw threaded section fixedly formed on the inner shaft proximally adjacent to the cutting edge, and the outer shaft fitting about and over the inner shaft and including a threaded distal end, the inner and outer shafts having structures on their proximal ends for use in maneuvering the shafts as necessary, independently of one another, and a laparoscope sized instrument head incorporating at a proximal end thereof, first needlescopic instrument engaging structure for engaging the threaded distal end of the outer shaft and second needlescopic instrument engaging structure for engaging the screw threaded portion of the inner shaft, the inner shaft extending further distally within the proximal end of the laparoscope sized instrument head, thereby creating a doubly engaged assembly comprising the needlescopic instrument and the laparoscope sized instrument head.

2. The assembly of claim 1 wherein the first and second engaging structures for engaging the threaded portions of the inner and outer shafts comprise a first and a second clips which engage threads of the threaded portions against disengagement upon exertion of a proximal pulling force.

3. The assembly of claim 1 wherein the distal end of the inner shaft is functionally engaged to a functional structure at the distal end of the laparoscope sized instrument head via clockwise threading of the threaded portion of the inner shaft thereto.

4. The assembly of claim 1 wherein the outer shaft is fixed against rotation by the first needlescopic instrument engaging structure in the laparoscope sized head engaging the shaft when the threaded distal end of the outer shaft is appropriately engaged by the structure engaging the threads thereof.

5. The assembly of claim 1 wherein the proximal end of the inner shaft is engaged to a handle for controlling insertion and extraction thereof and also to a rotation knob for controlling rotation of the inner shaft.

6. The assembly of claim 1 wherein the proximal end of the outer shaft is engaged to a control hub in fixed relationship thereto for controlling insertion and extraction and for controlling rotation of the outer shaft.

7. The assembly of claim 1 wherein the first and second needlescopic engaging structures are fixed in place within the laparoscope sized head.

8. The assembly of claim 1 wherein the outer shaft is rotatable into engagement with the proximal end of the laparoscope sized head so both rotate together until disengaged from one another.

9. The assembly of claim 2 wherein the engagement between first and second clips and the threaded portions of the inner and outer shafts thereof is confirmed by the sound of two clicks when the first and second clips each respectively engage with the threaded portions of the inner and outer shaft.

10. The assembly of claim 1, wherein:
the screw threaded section of the inner shaft is rotatable with the inner shaft to engage the second needlescopic instrument engaging structure of the laparoscope sized instrument head.

11. The assembly of claim 1, wherein:
the instrument head includes at least one lever arm receivable in a slot in the outer shaft; and
wherein when received in the slot, the lever arm prevents relative rotation between the outer shaft and the instrument head.

12. An assembly for use in needlescopic surgery, comprising:
an instrument having an inner shaft having a distal piercing tip and a first connection mechanism fixedly connected to the inner shaft and moveable therewith, and an outer shaft having a second connection mechanism, the outer shaft fitting about and over the inner shaft; and
an instrument head having a first engagement structure for engaging the first connection mechanism of the inner shaft, and a second engagement structure for engaging the second connection mechanism of the outer shaft;
wherein engagement of the first connection mechanism of the inner shaft with the first engagement structure of the instrument head, and engagement of the second connection mechanism of the outer shaft with the second engagement structure of the instrument head provides a redundant connection between the instrument and the instrument head.

13. The assembly of claim 12, wherein:
the first connection mechanism includes a first threaded portion on the inner shaft; and
the second connection mechanism includes a second threaded portion on the outer shaft.

14. The assembly of claim 13, wherein:
threads of the first threaded portion are oppositely threaded with respect to threads of the second threaded portion such that rotation of the inner shaft and rotation of the outer shaft in opposite directions is required to attach and/or detach the inner shaft and the outer shaft to or from the instrument head.

15. The assembly of claim 12, wherein
the instrument head includes at least one lever arm receivable in a slot in the outer shaft; and
wherein when received in the slot, the lever arm prevents relative rotation between the outer shaft and the instrument head.

16. An assembly for use in needlescopic surgery, comprising:
an instrument having an inner shaft having a distal piercing tip and a first connection mechanism, and an outer shaft having a second connection mechanism, the outer shaft fitting about and over the inner shaft; and
an instrument head having a first engagement structure for engaging the first connection mechanism of the inner shaft, and a second engagement structure for engaging the second connection mechanism of the outer shaft;
wherein engagement of the first connection mechanism of the inner shaft with the first engagement structure of the instrument head, and engagement of the second connection mechanism of the outer shaft with the second engagement structure of the instrument head provides a redundant connection between the instrument and the instrument head;
wherein the instrument head includes at least one lever arm receivable in a slot in the outer shaft; and
wherein when received in the slot, the lever arm prevents relative rotation between the outer shaft and the instrument head.

17. The assembly of claim 16, wherein:
the at least one lever arm is rotatable to a disengaged position whereby the lever arm is not received in the slot and the outer shaft is rotatable with respect to the instrument head.

* * * * *